(12) United States Patent
Kantor et al.

(10) Patent No.: US 6,613,930 B2
(45) Date of Patent: Sep. 2, 2003

(54) METHODS FOR PRODUCING 3-CYANO-AND 4-CYANO- BENZOIC ACID DERIVATIVE COMPOUNDS

(75) Inventors: James Kantor, San Francisco, CA (US); John Jason Gentry Mullins, San Francisco, CA (US); Robert Scarborough, Half Moon Bay, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 364 days.

(21) Appl. No.: 09/737,443

(22) Filed: Dec. 13, 2000

(65) Prior Publication Data

US 2002/0072626 A1 Jun. 13, 2002

Related U.S. Application Data

(60) Provisional application No. 60/170,400, filed on Dec. 13, 2000.

(51) Int. Cl.$^7$ .............................................. C07C 253/00
(52) U.S. Cl. ...................................................... 558/317
(58) Field of Search .......................................... 558/317

(56) References Cited

U.S. PATENT DOCUMENTS 5,618,843 A    4/1997   Fisher et al.
5,731,324 A    3/1998   Fisher et al.

OTHER PUBLICATIONS

Sasson Y et al. "Liquid–Phase Oxidation of Deactivated Methylbenzenes By Aqueous Sodium Hypochlorite Catalyzed By Ruthenium Salts Under Phase–Transfer Catalytic Conditions" *Journal of Organic Chemistry, American Chemical Society, Easton, US* vol. 51, 1986, pp. 2880–2883.

Paul Barraclough, et al. "An Adventitious Synthesis of a 5–Methylimidazo 4,5–Clpyridine Derivative" *Tetrahedron Letters*, vol. 27, No. 49, 1986, pp. 5997–6000 Elsevier Science Publishers, Amsterdam.

*Primary Examiner*—Joseph K. McKane
*Assistant Examiner*—Robert Shiao
(74) *Attorney, Agent, or Firm*—Knobbe, Martens, Olson & Bear, LLP

(57) ABSTRACT

Novel process steps and novel processes for producing unsubstituted and substituted meta- and para-cyano benzoic acid compounds, as well as salts and derivatives thereof, and intermediates therefor which are useful as intermediates for producing platelet aggregation inhibitors. Further disclosed are processes for producing bicyclic and heterocyclic cyano substituted compounds also having a carboxyl group attached to the same ring structure.

4 Claims, No Drawings

METHODS FOR PRODUCING 3-CYANO- AND 4-CYANO- BENZOIC ACID DERIVATIVE COMPOUNDS

CROSS-REFERENCE TO RELATED APPLICATION

This application claims benefit under 35 U.S.C. §119(e) of U.S. Provisional Application Ser. No. 60/170,400, filed Dec. 13, 2000.

FIELD OF THE INVENTION

This invention relates to novel processes for producing cyanobenzoic acid derivative compounds, salts thereof and intermediates therefor. The invention further relates to improved catalytic processes for making carboxylic acid derivatives from substituents on an unsaturated aryl compound.

BACKGROUND OF THE INVENTION

Known processes exist for making cyanobenzoic acid compounds, particularly 4-cyanobenzoic acid (CAS 619-65-8) and 2-fluoro-4-cyanobenzoic acid (benzoic acid 119, for example, in reaction Scheme 17 of U.S. Pat. No. 5,731,324, at pages 77–80) compounds from the corresponding 4-aminotoluene and 4-amino-2-fluorotoluene compounds. However, the starting materials for such process are often very expensive, have limited availability, and may be difficult to modify in a good yield. For example, 2-fluoro-4-cyanobenzoic acid can be prepared from 4-amino-2-fluorotoluene using standard methods in the presence of EDCI and DMAP, or the like. Often the yield for making derivatives, or the recovery of intermediates are difficult with respect to nitrites. Oxidation procedures to convert the methyl group of the toluene to a carboxylic acid group when the nitrile group is present on the aromatic ring often tend to have a relatively low yield and sometimes a complicated recovery and purification. When the presence of both a carboxylic acid group and the halogen group are desired on the ring, the procedures become even more difficult and the low yields are very common, which are not well tolerated. The yield is also complicated by the fact that the starting materials are also expensive. Therefore, there is a need for efficient processes to produce p- and m-cyanobenzoic acid derivatives (and the like with pyridyl derivatives) which are particularly substituted ortho to the carboxylic acid group with selected substituents, such as halogens, alcohols or ethers, which use economically priced starting materials and higher yielding overall steps than current processes, wherein the processes can be scaled to industrial levels with readily available materials and reagents. Such compounds, their intermediates and salts are useful as functional groups in a wide variety of industrial and pharmaceutical fields.

SUMMARY OF THE INVENTION

The present invention relates to novel processes for producing para or meta cyanobenzoic acid derivative compounds wherein up to four of the free hydrogens on the benzene ring may be replaced with a group such as I, F, Br, Cl, OH, O-alkyl and the like. Further, the process according to the invention provides processes for making the corresponding carboxyl substituted pyridyl compounds having a cyano group located ortho or meta with respect to the carboxyl group. Such functional group substituted phenyl and pyridyl compounds are intermediates for producing therapeutic agents, for example, for disease states in mammals that have disorders caused by or impacted by platelet dependent narrowing of the blood supply.

In accordance with one aspect of the present invention, there is provided a process for preparing derivatives of 4-cyanobenzoic acid. The process comprises contacting 2-amino-4-nitrotoluene with HR/NaNO$_3$ followed by heating to form 2-R-substituted 4-nitrotoluene:

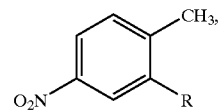

wherein R is hydrogen, alkyl, halo, or alkoxy, followed by exposing the above compound to reducing conditions to reduce the nitro group on the ring to form a 2-R-substituted 4-aminotoluene, contacting the reduced compound with NaNO$_2$/HCl followed by the addition of a source of cyanate ion to form 2-R-substituted 4-cyanotoluene, and oxidizing the methyl group of the cyano compound to form 2-R-substituted-4-cyanobenzoic acid.

In accordance with a further aspect of the present invention, there is provided an alternate method for preparing derivatives of 4-cyanobenzoic acid. The process comprises contacting 2-amino-4-nitrotoluene with HR/NaNO3 followed by heating to form 2-R-substituted 4-nitrotoluene:

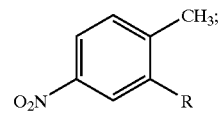

wherein R is hydrogen, alkyl, halo, or alkoxy, followed by exposing the above compound to oxidizing conditions to oxidize the methyl group on the ring to form 2-R-substituted 4-nitrobenzoic acid, hydrogenating the nitro group on the ring to form 2-R-substituted 4-aminobenzoic acid, and contacting the 2-R-substituted 4-aminobenzoic acid with NaNO$_2$/HCl followed by the addition of a source of cyanate ion to form a 2-R-substituted 4-cyanobenzoic acid derivative compound.

In accordance with another aspect of the present invention, there is provided a process for preparing derivatives of 3-cyanobenzoic acid. The process comprises contacting 2-amino-5-nitrotoluene with HR/NaNO$_3$ followed by heating to form 5-R-substituted 3-nitrotoluene:

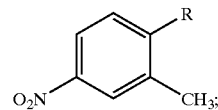

wherein R is hydrogen, alkyl, halo, or alkoxy, followed by hydrogenating the nitro group on the above compound to form 5-R-substituted 3-aminotoluene, contacting the 5-R-substituted 3-aminotoluene with NaNO$_2$/HCl followed by the addition of a source of cyanate ion to form 5-R-substituted 3-cyanotoluene, and oxidizing the methyl group on the ring to form 5-R-substituted 3-cyanobenzoic acid.

In accordance with a further aspect of the present invention, there is provided an alternate process for preparing derivatives of 3-cyanobenzoic acid. The process comprises contacting 2-amino-5-nitrotoluene with HR/NaNO$_3$ followed by heating to form 5-R-substituted 3-nitrotoluene:

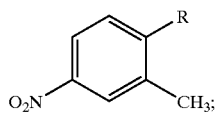

wherein R is hydrogen, alkyl, halo, or alkoxy, followed by oxidizing the methyl group on the ring to form 5-R-substituted 3-nitrobenzoic acid, hydrogenating the nitro group on the ring to form 5-R-substituted 3-aminobenzoic acid, and contacting the 5-R-substituted 3-aminobenzoic acid with NaNO₂/HCl followed by the addition of a source of cyanate ion to form 5-R-substituted 3-cyanobenzoic acid.

In accordance with yet another aspect of the present invention, there is provided a process for preparing 3-fluoro-4-cyanobenzoic acid. The process comprises contacting 2-chloro-4-nitrobenzoic acid with a metal fluoride to cause a halogen exchange to form 2-fluoro-4-nitrobenzoic acid; exposing the 2-fluoro-4-nitrobenzoic acid to reducing conditions to reduce the nitro group on the ring to form 2-fluoro-4-aminobenzoic acid; and contacting the 2-fluoro-4-aminobenzoic acid with NaNO₂/HCl followed by the addition of a source of cyanate ion to form 3-fluoro-4-cyanobenzoic acid.

DETAILED DESCRIPTION OF THE INVENTION

Preferred Embodiments

The processes of the present invention are directed to producing p- or m-cyanobenzoic acid derivative compounds wherein the up to four of the free hydrogens on the benzene ring may be replaced with a group such as I, F, Br, Cl, OH, O-alkyl and the like. The processes further provide for making the corresponding carboxyl substituted pyridyl compounds having a cyano group located ortho or meta with respect to the carboxyl group. Such functional group substituted phenyl and pyridyl compounds may be used as intermediates for producing therapeutic agents, for example, for disease states in mammals that have disorders caused by or impacted by platelet dependent narrowing of the blood supply.

In one aspect, the present invention provides a process to convert at least one amino group present on a benzene ring or phenyl ring to a hydrogen, halogen group, a hydroxyl group or an alkoxy group prior to the presence of a nitrile group on the ring. Preferably, a carboxyl group is present on the ring or a methyl group on the ring (tolyl or methyl pyridyl derivative) is oxidized to form a ring carboxyl group prior to the presence of a nitrile group on the ring as in Scheme II, but the oxidation may be done after the formation of the nitrile as in Scheme I. The oxidizing agent is preferably KMnO₄, a ruthenium derivative catalyst, an iridium derivative catalyst, or the like, wherein sodium hypochlorite (bleach) or the like is optionally present.

In another preferred aspect, the present invention provides a process for converting one or more amino groups on a phenyl or pyridyl ring into a diazonium compound, optionally in the presence of a tertiary amine or ammonia, and using a Sandmeyer procedure or the like to replace the diazonium compound with a desired ring substituent group prior to forming a nitrile (cyano group on the ring). For example, allowing the diazonium compound to warm up to room temperature or heating it will ordinarily result in its replacement with the halogen group utilized to form the diazonium compound. Preferably at least one nitro group is present as a substitutent on the ring during such replacement(s) of the amino group(s) via a diazonium derivative compound. In preferred embodiments, a methyl group or the like on the ring is oxidized to an aldehyde or carboxyl group prior to forming a nitrile (cyano group on the ring) as in Scheme IV, but the oxidation may be done after the formation of the nitrile as in Scheme III. Once formed, the carboxyl group on the ring can readily be converted to an ester, carboxamide derivative or the like, if such derivative is desired.

After one or both of the above two steps, a nitro group on the phenyl or pyridyl ring is hydrogenated, such as by Fe/HCl or SnCl₂/HCl, or by catalytic hydrogenation by use of catalysts such as palladium/carbon or nickel, and other such reductive methods. Essentially, most reducing catalysts will work under reasonably mild conditions to convert the nitro group to an amino group. The amino group is then converted to a diazonium compound, optionally in the presence of a tertiary amine or ammonia, and a nitrile is formed. Using a Sandmeyer procedure, or the like, the diazonium compound is replaced with a cyano group.

In another preferred aspect, a benzoic acid derivative containing a nitro group and a halogen group such as a chlorine group is first subjected to a halogen exchange reaction with a metal salt of a fluoride, such as potassium fluoride (KF), to obtain an benzoic acid derivative with a ring fluoro group in a desired position. The ring nitro group is then hydrogenated, e.g. by use of Fe/HCl or SnCl₂/HCl, or by catalytic hydrogenation by use of catalysts such as palladium/carbon or nickel, and other such reductive methods as described above, to convert it to an amino group. The amino group is then converted to a diazonium compound, optionally in the presence of a tertiary amine or ammonia, and a nitrile is formed. Using a Sandmeyer procedure, or the like, the diazonium compound is replaced with a cyano group.

The non-limiting reaction schemes below illustrate the processes according to preferred embodiments of the invention with respect to phenyl compounds, but also readily apply to pyridyl compounds, as well as other heterocylic compounds. The R substitutent in preferred embodiments set forth below which occurs on the phenyl ring is a halogen group which is utilized in the Sandmeyer procedure or a modified Sandmeyer procedure. Where the diazonium group is to be replaced with a hydroxyl group, this is accomplished by adding water to the reaction mixture prior to permitting the reaction mixture to warm to room temperature. Preferably, the reaction mixture is at about 0° C. when the water is added.

Scheme I is directed to the formation of para-cyano benzoic acid derivatives wherein the carboxyl group is formed after the cyano group is present on the phenyl ring and is as follows:

SCHEME I

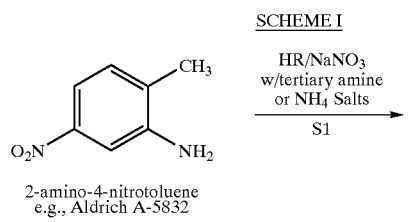

2-amino-4-nitrotoluene
e.g., Aldrich A-5832

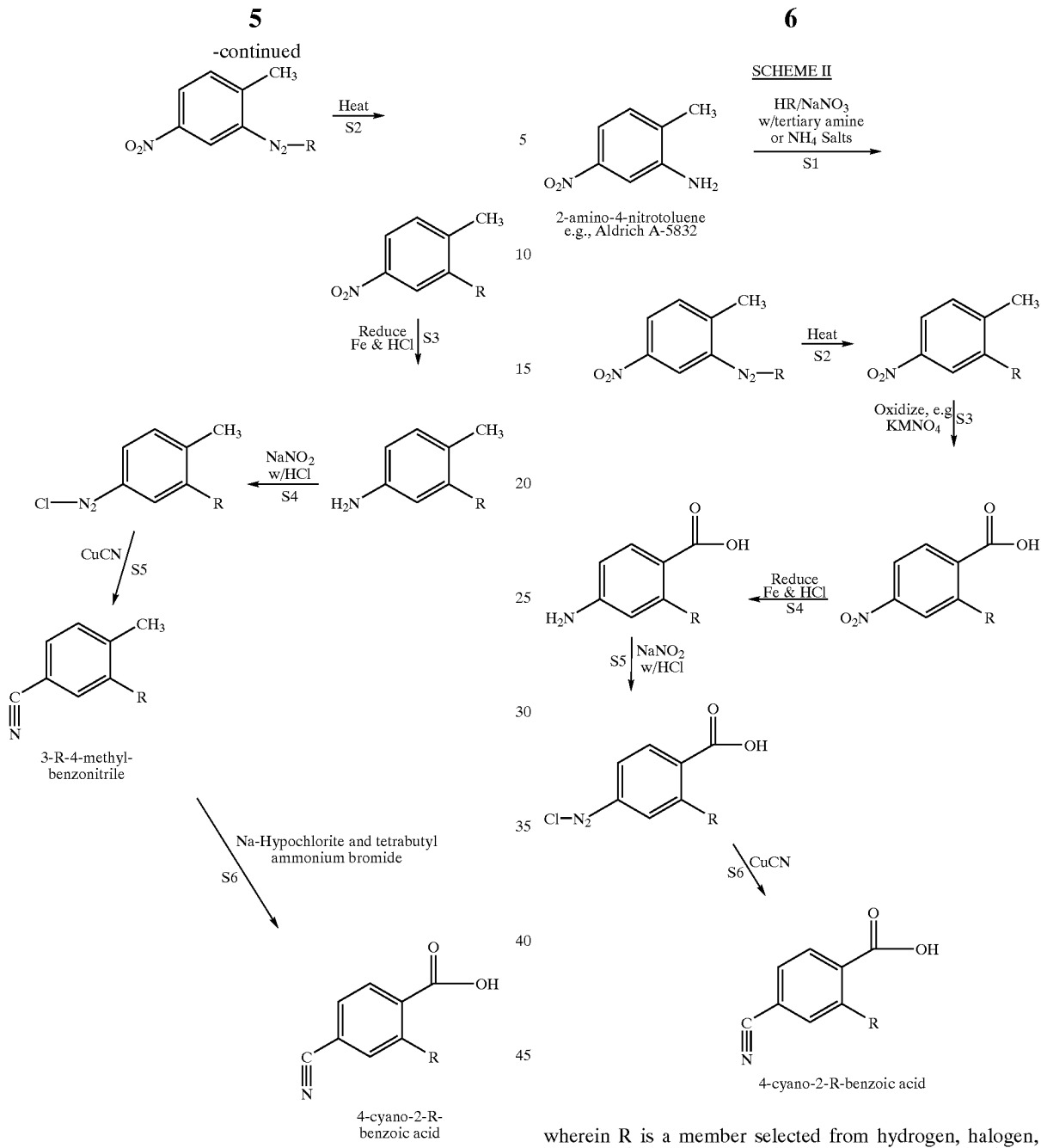

wherein R is a member selected from hydrogen, halogen, OH, OR' (wherein R' is alkyl or other lipophilic group). An acid addition salt, basic salt or the like may be formed of the carboxyl group, if desired. The formation of esters, acyl halides and carboxamides from the carboxyl group are contemplated. Such reactions may be accomplished by techniques known to those of skill in the art.

Scheme II is directed to the formation of p-cyanobenzoic acid derivatives wherein the carboxyl group is formed before a cyano group is present on the phenyl ring (i.e., carboxyl derivative is not also a nitrile), the process is generally as follows:

wherein R is a member selected from hydrogen, halogen, OH, OR' (wherein R' is alkyl or other lipophilic group). An acid addition salt, basic salt or the like may be formed of the carboxyl group, if desired. The formation of esters, acyl halides and carboxamides from the carboxyl group are contemplated. Such reactions may be accomplished by techniques known to those of skill in the art.

Scheme III is directed to the formation of m-cyanobenzoic acid derivatives wherein the carboxyl group is formed after the cyano group is present on the phenyl ring and is as follows:

SCHEME III

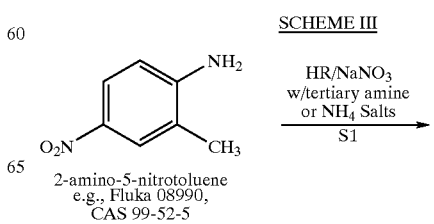

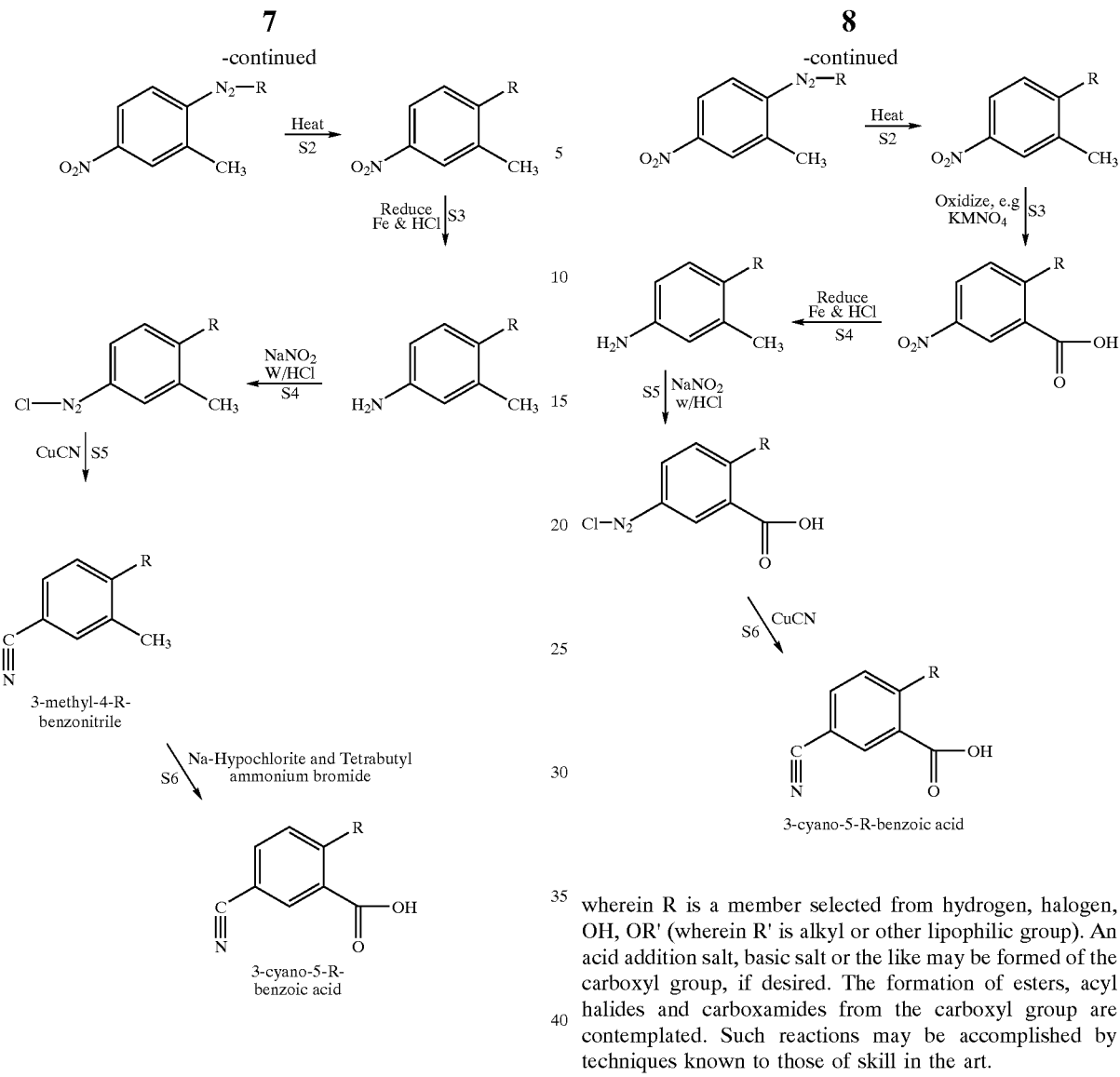

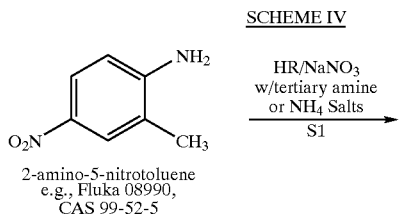

wherein R is a member selected from hydrogen, halogen, OH, OR' (wherein R' is alkyl or other lipophilic group). An acid addition salt, basic salt or the like may be formed of the carboxyl group, if desired. The formation of esters, acyl halides and carboxamides from the carboxyl group are contemplated. Such reactions may be accomplished by techniques known to those of skill in the art.

Scheme IV is directed to the formation of m-cyanobenzoic acid derivatives wherein the carboxyl group is formed before a cyano group is present on the phenyl ring (i.e., carboxyl derivative is not also a nitrile), the process is generally as follows:

wherein R is a member selected from hydrogen, halogen, OH, OR' (wherein R' is alkyl or other lipophilic group). An acid addition salt, basic salt or the like may be formed of the carboxyl group, if desired. The formation of esters, acyl halides and carboxamides from the carboxyl group are contemplated. Such reactions may be accomplished by techniques known to those of skill in the art.

Scheme V is directed to the formation of p-cyanobenzoic acid derivatives wherein the carboxyl group is already present and a halogen exchange reaction is conducted prior to forming a nitrile, the process is generally as follows:

SCHEME V

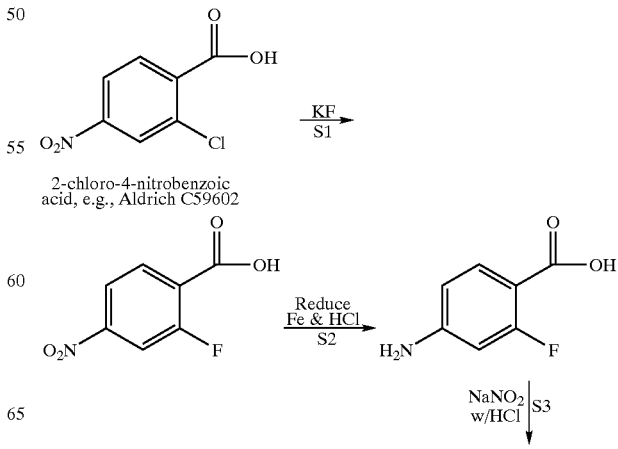

-continued

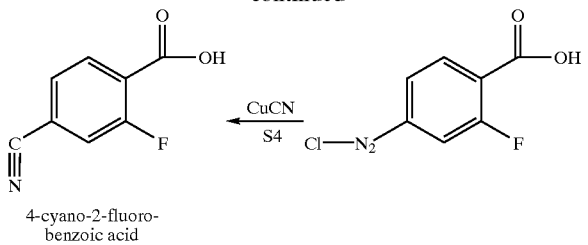

4-cyano-2-fluoro-
benzoic acid wherein R is a member selected from hydrogen, halogen, OH, OR' (wherein R' is alkyl or other lipophilic group). An acid addition salt, basic salt or the like may be formed of the carboxyl group, if desired. The formation of esters, acyl halides and carboxamides from the carboxyl group are contemplated. Such reactions may be accomplished by techniques known to those of skill in the art.

As mentioned above, the compounds of this invention find utility as intermediates for producing therapeutic agents or as therapeutic agents for the prevention or treatment of thrombosis, including conditions that are due to platelet-mediated narrowing of the blood supply, such as those which result from injury, surgical intervention or disease. Examples of such indications include, but are not limited to atherosclerosis and arteriosclerosis, acute myocardial infarction, chronic stable angina, unstable angina, transient ischemic attacks and strokes, cerebrovascular conditions, restenosis, peripheral vascular disease, arterial thrombosis, preclampsia, embolism, carotid endarterectomy, anastomosis of vascular grafts, and etc.

Platelet adhesion and aggregation is believed to be an important part of thrombus formation. This activity is mediated by a number of platelet adhesive glycoproteins. The binding sites for fibrinogen, fibronectin and other clotting factors have been located on the platelet membrane glycoprotein complex IIb/IIIa. When a platelet is activated by an agonist such as thrombin the GPIIb-IIIa binding site becomes available to fibrinogen, eventually resulting in platelet aggregation and clot formation. Thus, intermediate compounds for producing compounds that effective in the inhibition of platelet aggregation and reduction of the incidence of clot formation are useful intermediate compounds.

The compounds produced according to the present invention may also be used as intermediates in the formation of compounds that may be administered in combination or concert with other therapeutic or diagnostic agents. In certain preferred embodiments, the compounds produced by the intermediates according to the present invention may be co-administered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds produced from the intermediates according to the present invention may act in a synergistic fashion to prevent reocclusion following a successful thrombolytic therapy and/or reduce the time to reperfusion. Such compounds may also allow for reduced doses of the thrombolytic agents to be used and therefore minimize potential hemorrhagic side-effects. Such compounds can be utilized in vivo, ordinarily in mammals such as primates, (e.g. humans), sheep, horses, cattle, pigs, dogs, cats, rats and mice, or in vitro.

The nitrile compounds according to the present invention can be converted into amidino compounds as described at page 54, lines 16–23, of U.S. Pat. No. 5,731,324, for example. Namely, the nitrile compounds according to the invention may be (1) reacted with $H_2S$, (2) the resulting intermediate thioamide can be alkylated with methyl iodine, (3) the intermediate thioimidate can then be reacted with ammonium acetate to produce the amidino group. The amidino group may be optionally protected with a Boc protecting group, before or after reaction of the carboxyl group with another compound to produce a derivatized carboxyl group. The Boc protecting group is optionally removed from the amidino group by reacting the compound with neat TFA, before or after reaction of the carboxyl group with the other compound.

The starting materials used in above processes are commercially available from chemical vendors such as Aldrich, Sigma, Nova Biochemicals, Bachem Biosciences, and the like, or may be readily synthesized by known procedures, for example, by using procedures such as indicated above.

Reactions are carried out in standard laboratory glassware and reaction vessels under reaction conditions of standard temperature and pressure, except where otherwise indicated, or is well-known in literature available in the art. Further, the above procedures of the claimed invention processes my be carried out on a commercial scale by utilizing reactors and standard scale-up equipment available in the art for producing large amounts of compounds in the commercial environment. Such equipment and scale-up procedures are well-known to the ordinary practitioner in the field of commercial chemical production.

During the synthesis of these compounds, amino or acid functional groups may be protected by blocking groups to prevent undesired reactions with the amino group during certain procedures. Examples of suitable blocking groups are well know in the art. Further, removal of amino blocking groups by procedures such as acidification or hydrogenation are well-known in the art.

Five non-limiting exemplary synthesis schemes (I–V) shown above, which are each a preferred embodiment of the invention comprise the process steps outlined directly above. Further contemplated are processing steps which modify the cyano group to a desired functional group or couples the cyano compound to such groups as commonly described in the anti-coagulation field, as well as processing steps to modify or add substituents to the ring. In this respect, U.S. patent application Ser. No. 5,731,324 is incorporated herein in its entirety by reference. Phenyl groups are shown, but such processes can be readily adapted for bicyclic ring structures as well as heterocyclic ring structures that are common in the anti-coagulation field. Such structures are described in detail in U.S. Pat. Nos. 5,731,324 and 5,618,843, for example and are incorporated herein by reference. The reaction products are isolated and purified by conventional methods, typically by solvent extraction into a compatible solvent. Preferred solvents are lower alkane ethers and alcohols; ethyl ether and isopropyl alcohol, THF, ethyl acetate and the like, and ideal solvent(s) for solvent extraction or recrystallization procedures may be readily determined. The products may be further purified by column chromatography or other appropriate methods.

Salt Formation

Also described above, in a general fashion, is a process for the formation of acyl halides, esters or carboxamide groups from the benzoic acid carboxyl group as well as acid or base addition salts. In particular the mineral acid additions salts of the carboxyl group, such as the hydrochloride salt or hydrobromide salt, are envisioned. Other salts may be readily envisioned.

Coupling Reaction of the Hydrochloride Salt Intermediate Compounds

The above compounds produced according to the above invention may be isolated and further reacted to substitute a desired group for the hydroxyl portion of the carboxyl moiety or for one or more of the hydrogen atoms on the phenyl or aryl ring by a coupling reaction with the desired group. Particularly preferred is a coupling reaction an amino group on a chroman, chromone, thiochroman, thiochromone, quinoline, isoquinoline, which has a lipophilic moiety or another carbamimidoyl substituent directly or indirectly attached. For example, 5-cyano-thiophene 2-carboxylic acid derivatives (or an acid halide such as the acid chloride) which are made by the procedures set forth in one of reaction Schemes I–V, may be coupled to a hydrochloride salt of the amino group on an amino chromone to form 5-(5-cyano-2-thiophenoyl)-aminochromone derivatives, or other similar heteroaroyl or aroyl derivatives, which are known platelet aggregation inhibitors. For an example of such a platelet aggregation inhibitor having the 5-cyano-2-thiophenoyl-amino side group attached to a bicyclic core structure see U.S. Pat. No. 5,731,324, at pages 35–36, compound (LX). The ring portion of the above cyano-aroyl or cyano-heteroaroyl derivatives may be substituted by groups such as methyl, ethyl, fluoro, iodo, bromo, chloro, methoxy, ethyoxy, and the like which results in compounds that are known platelet aggregation inhibitors. Standard coupling procedures may be utilized, but procedures utilizing reaction mixtures wherein oxalyl chloride, toluene, DMF, pyridine and methylcyanide, or the like, are present are preferred for the coupling reaction. The resulting hydrochloride salt may be utilized or converted to the free base, which may itself be utilized or converted to salts of various inorganic and organic acids and bases. The production of such salts is within the scope of this invention. The free base or salts may be purified by various techniques such as recrystallization in a lower alkanol such as methanol, ethanol, propanol, isopropanol and the like, for example, or a mixture thereof. Preferably, the compound is recovered as the hydrochloride salt with an appropriate recrystallization. Non-toxic and physiologically compatible salts are particularly useful although other less desirable salts may have use in the processes of isolation and purification.

The compounds made by coupling an appropriate amino-substituted bicyclic structure with the cyanobenzoic acids produced according to the above invention, selected and used as disclosed herein or by reference, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboanginitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage. Thus the intermediates according to the present invention can be used to make compounds that can be added to or contacted with any medium containing or suspected to contain factor Xa and in which it is desired that blood coagulation be inhibited, e.g., when contacting the mammal's blood with material such as vascular grafts, stents, orthopedic prostheses, cardiac stents, valves and prostheses, extra corporeal circulation systems and the like.

Without further description, it is believed that one of ordinary skill in the art can, using the preceding description, fully practice the invention as set forth above and in the following claims. The preferred embodiments detailed above are non-limiting in that one of ordinary skill in view of the above will readily envision other permutations and variations on the invention without departing from the principal concepts and spirit of the invention. Such permutations and variations are also within the scope of the present invention.

What is claimed is:

1. A process for preparing derivatives of 4-cyanobenzoic acid, comprising (a) contacting 2-amino-4-nitrotoluene with HR/NaNO$_3$ followed by heating to make a compound having the formula:

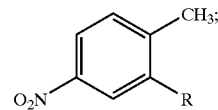

wherein R is hydrogen, alkyl, halo, or alkoxy;

(b) subjecting the compound from step (a) to a hydrogenation reaction to reduce the nitro group on the ring to form a compound having the formula:

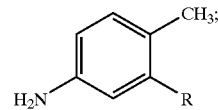

(c) contacting the compound from step (b) with NaNO$_2$/HCl followed by the addition of a source of cyanate ion to form a compound having the formula:

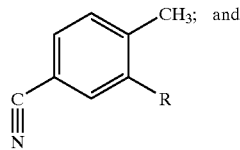

(d) exposing the compound from step (c) to oxidizing conditions to oxidize the methyl group on the ring to form a 4-cyanobenzoic acid derivative compound having the formula:

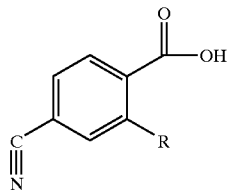

wherein R is hydrogen, alkyl, halo, or alkoxy.

2. A method according to claim 1, wherein the oxidizing conditions of step (d) comprise exposure to an oxidizing agent selected from the group consisting of potassium permanganate, ruthenium-derivative catalysts, and iridium-derivative catalysts.

3. A method according to claim 1, wherein the hydrogenation in step (b) is performed by exposure to a metal in acidic solution or exposure to $H_2$ under pressure in the presence of a hydrogenation catalyst.

4. A method according to claim 3, wherein the hydrogenation in step (b) is performed by use of Fe/HCl, $SnCl_2$/HCl, $H_2$/Pd/C, or $H_2$/Ni.

* * * * *